United States Patent [19]
Syed et al.

[11] Patent Number: 5,641,478
[45] Date of Patent: Jun. 24, 1997

[54] HAIR STRENGTHENING METHOD

[75] Inventors: Ali N. Syed, Orland Park; Kaleem Ahmad, Chicago, both of Ill.

[73] Assignee: Avlon Industries, Inc., Bedford Park, Ill.

[21] Appl. No.: 493,491

[22] Filed: Jun. 22, 1995

Related U.S. Application Data

[62] Division of Ser. No. 292,107, Aug. 17, 1994, Pat. No. 5,639,449.

[51] Int. Cl.$^6$ ............................................. A61K 7/09
[52] U.S. Cl. .................. 424/70.17; 132/202; 424/70.4; 424/70.11
[58] Field of Search ....................... 424/70.2, 70.4, 424/70.11, 70.17; 132/202, 204

[56]  References Cited

U.S. PATENT DOCUMENTS

| | | | |
|---|---|---|---|
| 3,811,835 | 5/1974 | Gallup et al. | 8/127.6 |
| 3,954,113 | 5/1976 | Bohrer et al. | 132/200 |
| 4,299,817 | 11/1981 | Hannan, III et al. | 424/70.13 |
| 4,319,020 | 3/1982 | Coscia et al. | 528/405 |
| 4,397,322 | 8/1983 | Arbaczawski | 132/202 |
| 4,579,131 | 4/1986 | Syed | 132/202 |
| 4,943,430 | 7/1990 | Hefford et al. | 424/70.6 |
| 5,037,818 | 8/1991 | Sime | 514/183 |
| 5,060,680 | 10/1991 | Akhtar | 132/204 |
| 5,077,042 | 12/1991 | Darkwa et al. | 424/70.2 |
| 5,147,635 | 9/1992 | Jachowicz et al. | 424/70.16 |
| 5,149,752 | 9/1992 | Jachowicz et al. | 526/240 |
| 5,338,540 | 8/1994 | Lee et al. | 424/70.4 |
| 5,476,650 | 12/1995 | Patel | 424/70.2 |

*Primary Examiner*—Melvyn I. Marquis
*Assistant Examiner*—Robert H. Harrison
*Attorney, Agent, or Firm*—Gardner, Carton & Douglas

[57]  ABSTRACT

A method of strengthening hair in need of strengthening includes the steps of applying a hair swelling component to the hair and applying a cationic polymer that is the reaction product of a lower dialkylamine ($C_1$–$C_3$), a difunctional epoxy-type reactant and a third reactant selected from the group consisting of ammonia, primary amines, alkylene diamines having two to six carbon atoms and polyamines to the hair.

8 Claims, No Drawings

HAIR STRENGTHENING METHOD

This application is a division of application Ser. No. 08/292,107, filed on Aug. 17, 1994, now U.S. Pat. No. 5,639,449.

TECHNICAL FIELD

This invention generally relates to strengthening hair. More particularly, the invention relates to a composition and method for strengthening hair that has been exposed to a relaxer.

BACKGROUND OF THE INVENTION

Human hair has a variety of textures, from fine to coarse and from straight to very curly. Hair is made of keratin which in turn is made of polypeptide chains bonded together by cystine (or disulfide) bonds, hydrogen bonds and salt linkages. The cortex is the inner part of the hair.

Curly hair is made of hair strands that have irregular surfaces that mesh and tangle with each other to make combing more difficult. Among individuals with excessively curly hair, e.g., individuals of African or Middle Eastern descent, it is especially popular to relax or straighten hair to increase hair manageability and ease of styling. The hair to be relaxed is either pressed or exposed to a relaxer that chemically transforms cystine bonds of the hair to lanthionine bonds. For this reason, the term for the chemical relaxing process is lanthionization.

During chemical relaxing, the hair is wetted with the relaxer and repeatedly smoothed and sometimes partially combed. Typical relaxers contain an alkali metal hydroxide or guanidine hydroxide as an active ingredient. The relaxers greatly decrease the tensile strength of the hair making it more likely to break. Hair being relaxed that is still wet loses as much as 45–50 percent (%) of the hair's original tensile strength. Relaxed hair that is dry loses about 20–25% of the hair's original tensile strength. It is presently theorized that the decrease in tensile strength is due to structural damage associated with $\alpha$-helical deformation which occurs during relaxing.

The $\alpha$-helical deformation of hair can occur under the following conditions:

a) When the high alkalinity relaxers degrade cystine bonds of the $\alpha$-keratine during straightening, partial deformation of the $\alpha$-helix becomes a reality which causes the loss of tensile strength in the hair fibers.

b) Partial deformation of $\alpha$-helix could be caused by the mechanical extension of hair fibers beyond yield and post-yield region which may not be reversible, even when the fibers are allowed to relax, i.e., rest in water.

c) During relaxing, degradation of cystine bonds and low level of mechanical force applied while applying and smoothing relaxer cream on hair causes the deformation of $\alpha$-helix in keratine fibers.

In chemical relaxing, once the desired degree of straightening is achieved, the relaxer is rinsed from the hair with water. The hair is then cleansed using a low pH, acidic nondetangling shampoo which is known as a neutralizing shampoo. After shampooing, the hair is very raspy in nature and rough to the touch.

Conditioners are often applied to the hair after shampooing to soften the hair. Quaternary ammonium compounds having chain lengths of about 11 to about 18 carbon atoms are often a component of these conditioners. Unfortunately, most of these compounds do not work when exposed to the relaxer or shampoo, and, therefore, they can only be used in post-shampooing conditioners. For example, U.S. Pat. Nos. 5,060,680 and 5,148,822, both to Akhtar, disclose straightening hair by a method that requires removing substantially all of the relaxer from the hair prior to applying an aqueous hair texturing and strengthening composition to the hair. Furthermore, these compounds do not strengthen hair when incorporated into the relaxer.

It is, therefore, an object of the present invention to provide an improved hair strengthening composition and easy-to-use method for strengthening hair.

SUMMARY OF THE INVENTION

The present invention provides an improved composition and method for strengthening hair. The composition and method are particularly useful for strengthening human hair straightened by a high alkalinity relaxer. The present composition and method strengthen the hair even in the presence of the relaxer.

According to the invention, a composition for treating hair includes a hair swelling component and a cationic polymer in an amount effective to strengthen the hair. The hair swelling component is preferably the high alkalinity hair relaxer. The hair strengthening cationic polymer is a water-dispersible polyquaternary ammonium polymer that is the reaction product of a lower dialkylamine ($C_1$–$C_3$), a difunctional epoxy-type reactant and a third reactant selected from the group consisting of ammonia, primary amines, alkylene diamines having two to six carbon atoms and polyamines.

The method includes the steps of applying a hair swelling component to hair in need of strengthening and applying the cationic polymer to hair.

It is presently theorized that the hair swelling component swells the hair to permit the cationic polymer to be affixed to the swollen hair, preferably to the hair cortex. The affixed cationic polymer remains on or in the hair even after the hair swelling component and cationic polymer that is not affixed are removed.

DETAILED DESCRIPTION OF THE PREFERRED EMBODIMENTS

A hair strengthening composition includes a hair swelling component and a cationic polymer.

The hair swelling component is capable of swelling the hair to facilitate the cationic polymer to be affixed to the swollen hair. A preferred hair swelling component is a high alkalinity hair relaxer that can have a pH in the range of about 11 to about 13.5.

The high alkalinity hair relaxer can be a multi-part hair relaxer system or a single part hair relaxer. Multi-part relaxer systems having two parts are known wherein the active hair relaxing ingredient, e.g., guanidine hydroxide, is generated in situ by the combination of the two parts. Typically, the multi-part relaxer system includes a cream relaxer as part A and a liquid activator as part B. Preferably, the cationic polymer is a component of the cream relaxer. Also present in the cream relaxer is one precomponent of the active hair relaxing ingredient. A preferred precomponent is a hydroxide such as an alkaline earth hydroxide, e.g., calcium hydroxide. The liquid activator contains a second precomponent of the active hair relaxing ingredient, such as those disclosed in U.S. Pat. No. 4,314,572 to de la Guardia. The de la Guardia patent and all other patents, articles and the like referred to or otherwise identified in this specification are incorporated herein by reference in their entirety. A preferred second precomponent is guanidine carbonate. When parts A and B are mixed together, the calcium hydroxide and the guanidine carbonate react with the reaction product being produce guanidine hydroxide, the active hair relaxing ingredient. The cream relaxer, Part A, may also include additional conventional components. The liquid activator, Part B, typically also includes deionized water.

The single part hair relaxer preferably uses a hydroxide such as an alkali metal hydroxide, e.g., sodium hydroxide, as the active hair relaxing ingredient. The remaining components of the single part hair relaxer are conventional.

The hair strengthening cationic polymer is described in more detail in U.S. Pat. No. Re. 28,808 to Panzer et al and U.S. Pat. No. 4,661,259 to Walterick et al. and is referred to in the '259 patent as a group (II) cationic polymer at column 3, lines 43 et seq. The cationic polymer is a water-dispersible polyquaternary polymer that is the reaction product of a lower dialkylamine ($C_1$–$C_3$), a difunctional epoxy-type reactant and a third reactant selected from the group consisting of ammonia, primary amines, alkylenediamines having two to six carbon atoms and polyamines.

Representative epoxy-type reactants include epihalohydrins, e.g., epichlorohydrin and epibromohydrin with epichlorohydrin being the preferred epihalohydrin, diepoxides, e.g., 1,4-butanediol-diglycidyl ethers, and precursors of epihalohydrins and diepoxides, e.g., 1,3-dichloropropanol-2 and 1,4-dichloro-2,3-dihydroxybutane.

Representative polyamines include polyalkylpolyamines having the structure disclosed in the '259 patent at column 3, lines 64 et seq.

The exact reaction parameters for the cationic polymer are specified in the '808 reissue patent and need not be repeated herein.

The preferred cationic polymer is the reaction product of a secondary amine and epihalohydrin in the presence of a small amount of ethylenediamine. See, for instance, EXAMPLE 2 of the '808 reissue patent.

It is presently theorized that the preferred cationic polymer has the following structure:

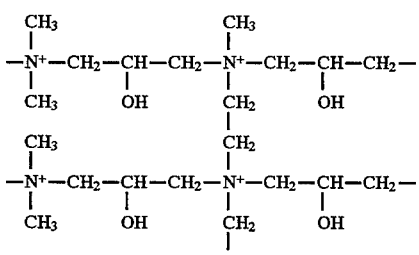

The molecular weight of the cationic polymer is in the range of about $400\times10^3$ to about $1\times10^6$ with the molecular weight of the preferred cationic polymer being in the range of about $400$–$600\times10^3$.

The cationic polymer in admixture with water is commercially available from Betz Laboratories, Trevose, Pa. under the designation Betz polymer 1195. The Betz polymer 1195 typically contains about 50 weight percent (wt %) of the cationic polymer and has an activity of about fifty percent.

The hair swelling component is present in the hair strengthening composition in an amount in the range of about 95 to about 99.5 wt % based upon the total weight of the hair-strengthening composition. The cationic polymer is present in an amount in the range of about 0.5 to about 5 wt %.

The method of strengthening hair in need of strengthening includes the steps of applying the hair swelling component to the hair and applying the cationic polymer. Preferably, the applying steps are performed simultaneously. The hair is preferably contacted with the hair swelling component for a time period sufficient to swell the hair. Some of the cationic polymer becomes affixed to the swollen hair. An aliquot of the cationic polymer can be affixed by penetrating the swollen hair, especially the cortex of the hair. The cationic polymer that is not affixed can be removed as by rinsing the hair with water. The hair swelling component can also be removed, or can be neutralized, using water or a conventional neutralizer.

The following tests were used to determine the efficacy of the hair strengthening composition containing a relaxer as the hair swelling component and the cationic polymer on wet and dry hair fibers.

Wet Hair Fibers

To determine the efficacy of the hair strengthening composition on wet hair fibers, twelve inch long European dark brown hair, commercially available from DeMeo Brothers, New York is washed with a mild shampoo containing 10% ammonium lauryl sulfate. The hair fibers are rinsed with tepid tap water for about two minutes and dried overnight at ambient temperature, i.e., a temperature in the range of about 20° to about 30° C. Twenty-five shampooed fibers having approximately the same diameter, i.e. a diameter in the range of about 71 to about 80 microns, are selected and then each fiber is cut into two halves. The hair fibers with the root end of the hair are identified as Group A, fibers 1–25, and are used as a control which is only treated with the relaxer. The hair fibers having the tip end are identified as Group B, fibers 26–50, and are treated with either the strengthening composition containing the relaxer and the strengthening cationic polymer or the relaxer and a comparison, nonstrengthening cationic polymer. The root end of the hair fibers is known to be slightly stronger than the tip end because the root end has had less exposure to damaging conditions. Therefore, one would expect that the length of hair having the root end would have a higher tensile strength than the hair fiber having the tip end. The Group A and B hair fibers are then immersed in tap water for at least 30 minutes.

The initial work done to extend the hair fibers 20% of their original length of 30 millimeters (mm) is conventionally referred to as an F20 Index Study and is determined using a conventional Dia-Stron MTT under conditions well known to those skilled in the art. The value of the initial work done to achieve 20% elongation is equal to X. The hair fibers of each group are then immersed in separate containers of water and allowed to recover overnight in the water. After recovering, the hair fibers are mounted on separate rectangular processing slabs and dried at ambient temperature for 30 minutes before treatment with the relaxer (Group A) or treatment with the strengthening composition or the relaxer and comparison polymer (Group B) for 18 minutes. The hair fibers are rinsed with tepid tap water for three minutes, treated with diluted nonconditioning neutralizing shampoo for three minutes, rinsed with tepid tap water for one minute, unmounted and stored overnight in water. The hair fibers are then elongated 20% using the Dia-Stron MTT while being periodically immersed in the water. Immersion is accomplished by mounting each end of a hair fiber sample into the holding clamps of a remote measurement jig for movement into and out of a water-filled compartment. The value of the work done after treatment with the relaxer to achieve 20% elongation is equal to Y. The F20 Index is determined using the following Equation I:

$$F20 \text{ Index} = [(X-Y)/X] \times 100 \qquad \text{I.}$$

Dry Hair Fibers

The above-described Group A and B hair fibers are equilibrated at 65% relative humidity and 21° C. overnight before determining the work required to extend them 20% of their original length. The initial work done to achieve 20% elongation of the equilibrated hair fibers is determined using the Dia-Stron MTT at the above-described parameters. The value of the initial work done is equal to X. After testing, the hair fibers are immersed in water and allowed to recover overnight. The hair fibers are then mounted by group on separate rectangular processing slabs and dried for 30 minutes at ambient temperature. The hair fibers are then treated with a relaxer (Group A) or with the strengthening composition or the relaxer and comparison polymer (Group B) for 18 minutes. The hair fibers are then rinsed with tepid tap water for three minutes, treated with diluted nonconditioning neutralizing shampoo for three minutes, rinsed with tepid tap water for one minute, unmounted, stored in water for one hour and transferred to an environmental room at 65% relative humidity and 21° C. overnight. The dry hair fibers are then elongated 20% using the Dia-Stron MTT at the above-described test parameters to determine the work done after treatment with the relaxer. The value of the work done after treatment is equal to Y. The F20 Index is then determined using the above-described Equation I.

The relaxers, hair strengthening compositions and comparison polymer-containing relaxers used in the examples had the compositions provided in TABLES 1 and 2, below.

TABLE 2

| Sodium Hydroxide-Containing Relaxers | | |
|---|---|---|
| Ingredients | Control Relaxer (Wt %) | Hair Strenthening Composition (Wt %) |
| Deionized Water | 55.03 | 53.03 |
| Propylene Glycol | 2.00 | 2.00 |
| Sodium Hydroxide (50%) | 4.50 | 4.50 |
| PEG-50 Lanolin | 0.49 | 0.49 |
| Betz Polymer 1195 | — | 2.00 |
| Petrolatum | 12.00 | 12.00 |
| Mineral Oil | 17.00 | 17.00 |
| Emulsifying Wax | 10.00 | 10.00 |
| Laneth-15 | 0.98 | 0.98 |

The following examples are given by way of illustration and not limitation. In the following examples, if the coefficient of variance is considerably above 10, it is advisable to eliminate fibers with unusually low or high average work done to bring the coefficient of variance up to 10. Therefore, those fibers were eliminated to bring down the coefficient of variance into the desirable range.

EXAMPLE I

Determination of F20 Index for Wet Fibers Treated with a Guanidine Relaxer and Hair Strengthening Composition Including a Guanidine Relaxer The F20 Index was determined using the procedure described above under the "WET HAIR FIBER" heading and the control guanidine relaxer and the Betz polymer 1195-containing hair strengthening composition of TABLE 1, above. The test results are provided in TABLES 3 and 4, below.

TABLE 1

| | Guanidine-Containing Relaxers | | | |
|---|---|---|---|---|
| Containing | Control Relaxer | Hair Strengthening | Merquat 100 - Polycare 133 - Containing | |
| Components (Wt %) | (Wt %) | Composition (Wt %) | Relaxer (Wt %) | Relaxer |
| PART A: Cream | | | | |
| Deionized Water | 50.73 | 48.33 | 47.73 | 47.09 |
| Propylene Glycol | 2.00 | 2.00 | 2.00 | 2.00 |
| Calcium Hydroxide | 5.50 | 5.50 | 5.50 | 5.50 |
| PEG-75 Lanolin | 2.25 | 2.25 | 2.25 | 2.25 |
| Betz Polymer 1195 (50%) | — | 2.40 | — | — |
| Merquat 100 (40%) | — | — | 3.00 | — |
| Polycare 133 (33%) | — | — | — | 3.64 |
| Petrolatum | 12.00 | 12.00 | 12.00 | 12.00 |
| Mineral Oil | 18.00 | 18.00 | 18.00 | 18.00 |
| Fatty Alcohol | 8.00 | 8.00 | 8.00 | 8.00 |
| Ceteth-20 | 1.50 | 1.50 | 1.50 | 1.50 |
| Mazu DF 200S | 0.02 | 0.02 | 0.02 | 0.02 |
| PART B: Liquid Activator | | | | |
| Guanidine Carbonate | 25.00 | | | |
| Deionized Water | 75.00 | | | |

TABLE 3

Group A Wet Fibers: Control, Treated With
Guanidine Relaxer Without Cationic Polymer

| Fiber No. | Initial Work Done* (X) | Work Done* After Relaxer (Y) | F20 Index After Relaxer Treatment (% Loss in Tensile Strength) |
|---|---|---|---|
| 1 | 1.150 | 0.541 | 52.96 |
| 2 | 1.390 | 0.687 | 50.58 |
| 3 | 1.500 | 0.714 | 52.40 |
| 4 | 1.470 | 0.662 | 54.97 |
| 6 | 1.370 | 0.607 | 55.69 |
| 7 | 1.520 | 0.784 | 48.42 |
| 9 | 1.270 | 0.595 | 53.15 |
| 11 | 0.939 | 0.432 | 53.99 |
| 12 | 1.180 | 0.461 | 60.93 |
| 13 | 1.090 | 0.519 | 52.39 |
| 14 | 1.430 | 0.694 | 51.47 |
| 15 | 1.170 | 0.613 | 47.61 |
| 17 | 0.921 | 0.414 | 55.05 |
| 18 | 0.992 | 0.501 | 49.50 |
| 19 | 1.290 | 0.677 | 47.52 |
| 20 | 1.220 | 0.632 | 48.20 |
| 21 | 1.180 | 0.573 | 51.44 |
| 22 | 1.170 | 0.605 | 48.29 |
| 23 | 1.410 | 0.725 | 48.58 |
| 25 | 1.120 | 0.542 | 51.61 |
| AVERAGE | | | 51.74 |
| STANDARD DEVIATION (SAMPLE) | | | 3.39 |
| COEFFICIENT OF VARIANCE | | | 6.54 |

*WORK DONE IS IN MILLIJOULES
The standard deviation is for the sample of data.
The coefficient of variance is determined by the following Equation II:
II. Coefficient of Variance = (Standard Deviation/Average) × 100

TABLE 4

Group B Wet Fibers: Experimental, Treated With
Guanidine Relaxer and Cationic Polymer Betz 1195

| Fiber No. | Initial Work Done* (X) | Work Done* After Relaxer (Y) | F20 Index After Relaxer Treatment (% Loss in Tensile Strength) |
|---|---|---|---|
| 26 | 1.040 | 0.513 | 50.67 |
| 27 | 1.640 | 0.950 | 42.07 |
| 28 | 1.440 | 0.819 | 43.13 |
| 29 | 1.190 | 0.668 | 43.87 |
| 30 | 1.430 | 0.842 | 41.12 |
| 31 | 1.290 | 0.636 | 50.70 |
| 34 | 1.270 | 0.706 | 44.41 |
| 35 | 1.250 | 0.757 | 39.44 |
| 36 | 0.816 | 0.429 | 47.43 |
| 37 | 1.110 | 0.562 | 49.37 |
| 38 | 1.010 | 0.589 | 41.68 |
| 39 | 1.370 | 0.767 | 44.01 |
| 41 | 1.160 | 0.646 | 44.31 |
| 42 | 0.956 | 0.454 | 52.51 |
| 44 | 1.210 | 0.659 | 45.54 |
| 45 | 1.240 | 0.688 | 44.52 |
| 46 | 1.060 | 0.461 | 56.51 |
| 47 | 1.100 | 0.617 | 43.91 |
| 48 | 1.090 | 0.513 | 52.94 |
| 50 | 1.050 | 0.517 | 50.76 |
| AVERAGE | | | 46.44 |
| STANDARD DEVIATION (SAMPLE) | | | 4.63 |
| COEFFICIENT OF VARIANCE | | | 9.96 |

*WORK DONE IS IN MILLIJOULES

As can be seen from TABLES 3 and 4, the average tensile strength loss was more than 11% less for the wet hair fibers treated with the hair strengthening composition of the present invention as compared to those treated with the Control. This reduction in loss of tensile strength means that the hair fibers are stronger and less prone to damage and breakage as compared to hair treated with the Control.

EXAMPLE II

Determination of F20 Index for Dry Fibers Treated with a Guanidine Relaxer and a Hair Strengthening Composition Including a Guanidine Relaxer The F20 Index was determined using the procedure described above under the "DRY HAIR FIBER" heading and the control guanidine relaxer and the Betz polymer 1195-containing hair strengthening composition of TABLE 1, above. The test results are provided in TABLES 5 and 6, below.

TABLE 5

Group A Dry Fibers: Control, Treated With
Guanidine Relaxer Without Cationic Polymer

| Fiber No. | Initial Work Done* (X) | Work Done* After Relaxer (Y) | F20 Index After Relaxer Treatment (% Loss in Tensile Strength) |
|---|---|---|---|
| 1 | 2.570 | 1.910 | 25.68 |
| 3 | 1.950 | 1.510 | 22.56 |
| 5 | 2.640 | 1.980 | 25.00 |
| 6 | 2.890 | 2.240 | 22.49 |
| 9 | 2.830 | 2.140 | 24.38 |
| 15 | 1.970 | 1.470 | 25.38 |
| 16 | 2.860 | 2.060 | 27.97 |
| 17 | 3.190 | 2.360 | 26.02 |
| 18 | 1.970 | 1.460 | 25.89 |
| 19 | 3.030 | 2.350 | 22.44 |
| 23 | 1.750 | 1.340 | 23.43 |
| AVERAGE | | | 24.66 |
| STANDARD DEVIATION (SAMPLE) | | | 1.78 |
| COEFFICIENT OF VARIANCE | | | 7.21 |

*WORK DONE IS IN MILLIJOULES

TABLE 6

Group B Dry Fibers: Experimental, Treated With
Guanidine Relaxer and Cationic Polymer Betz 1195

| Fiber No. | Initial Work Done* (X) | Work Done* After Relaxer (Y) | F20 Index After Relaxer Treatment (% Loss in Tensile Strength) |
|---|---|---|---|
| 26 | 2.590 | 2.030 | 21.62 |
| 27 | 3.040 | 2.420 | 20.39 |
| 28 | 2.540 | 1.990 | 21.65 |
| 35 | 3.020 | 2.390 | 20.86 |
| 37 | 2.990 | 2.250 | 24.75 |
| 40 | 2.250 | 1.680 | 25.33 |
| 41 | 3.110 | 2.350 | 24.44 |
| 42 | 2.980 | 2.280 | 23.49 |
| 44 | 3.100 | 2.360 | 23.87 |
| 49 | 2.540 | 2.000 | 21.26 |
| 50 | 2.610 | 2.070 | 20.69 |
| AVERAGE | | | 22.58 |
| STANDARD DEVIATION (SAMPLE) | | | 1.82 |
| COEFFICIENT OF VARIANCE | | | 8.05 |

*WORK DONE IS IN MILLIJOULES

As can be seen from TABLES 5 and 6, the average tensile strength loss was more than 9% less for the dry hair fibers treated with the hair strengthening composition of the present invention as compared to those treated with the Control. This reduction in loss of tensile strength means that the hair fibers are stronger and less prone to damage and breakage as compared to hair treated with the Control.

EXAMPLE III

Determination of F20 Index for Wet Fibers Treated with a Sodium Hydroxide Relaxer and a Hair Strengthening Composition Including a Sodium Hydroxide Relaxer The F20 Index was determined using the procedure described above under the "WET HAIR FIBER" heading and the control sodium hydroxide relaxer and the Betz polymer 1195-containing hair strengthening composition of TABLE 2, above. The test results are provided in TABLES 7 and 8, below.

TABLE 7

Group A Wet Fibers: Control, Treated With Sodium Hydroxide Relaxer Without Cationic Polymer

| Fiber No. | Initial Work Done* (X) | Work Done* After Relaxer (Y) | F20 Index After Relaxer Treatment (% Loss in Tensile Strength) |
|---|---|---|---|
| 3 | 1.540 | 0.966 | 37.27 |
| 4 | 1.210 | 0.660 | 45.45 |
| 5 | 1.360 | 0.738 | 45.74 |
| 6 | 1.260 | 0.711 | 43.57 |
| 8 | 1.290 | 0.697 | 45.97 |
| 12 | 1.520 | 0.958 | 36.97 |
| 13 | 1.420 | 0.756 | 46.76 |
| 15 | 0.944 | 0.571 | 42.56 |
| 16 | 0.895 | 0.512 | 42.79 |
| 17 | 1.040 | 0.581 | 44.13 |
| 18 | 1.310 | 0.796 | 39.24 |
| 19 | 1.110 | 0.650 | 41.44 |
| 23 | 1.640 | 0.964 | 41.22 |
| 25 | 1.080 | 0.588 | 45.56 |
| AVERAGE | | | 42.76 |
| STANDARD DEVIATION (SAMPLE) | | | 3.20 |
| COEFFICIENT OF VARIANCE | | | 7.48 |

*WORK DONE IS IN MILLIJOULES

TABLE 8

Group B Wet Fibers: Experimental, Treated With Sodium Hydroxide Relaxer and Cationic Polymer Betz 1195

| Fiber No. | Initial Work Done* (X) | Work Done* After Relaxer (Y) | F20 Index After Relaxer Treatment (% Loss in Tensile Strength) |
|---|---|---|---|
| 27 | 1.080 | 0.734 | 32.04 |
| 30 | 1.240 | 0.949 | 31.53 |
| 33 | 1.340 | 0.884 | 34.03 |
| 35 | 0.755 | 0.526 | 30.33 |
| 37 | 1.340 | 0.934 | 30.30 |
| 38 | 1.300 | 0.855 | 34.23 |
| 39 | 1.230 | 0.865 | 29.67 |
| 40 | 0.875 | 0.549 | 37.26 |
| 41 | 0.820 | 0.490 | 40.24 |
| 42 | 1.090 | 0.707 | 35.14 |
| 44 | 1.070 | 0.727 | 32.06 |
| 46 | 1.240 | 0.851 | 31.37 |
| 47 | 1.140 | 0.675 | 40.79 |
| 48 | 1.660 | 1.040 | 37.35 |
| AVERAGE | | | 34.02 |
| STANDARD DEVIATION (SAMPLE) | | | 3.67 |
| COEFFICIENT OF VARIANCE | | | 10.78 |

*WORK DONE IS IN MILLIJOULES

As can be seen from TABLES 7 and 8, the average tensile strength loss was more than 25% less for the wet hair fibers treated with the hair strengthening composition of the present invention as compared to those treated with the Control. This reduction in loss of tensile strength means that the hair fibers are stronger and less prone to damage and breakage as compared to hair treated with the Control.

EXAMPLE IV

Determination of F20 Index for Dry Fibers Treated with a Sodium Hydroxide Relaxer and a Hair Strengthening Composition Including a Sodium Hydroxide Relaxer The F20 Index was determined using the procedure described above under the "DRY HAIR FIBER" heading and the control sodium hydroxide relaxer and the Betz polymer 1195-containing hair strengthening composition of TABLE 2, above. The test results are provided in TABLES 9 and 10, below.

TABLE 9

Group A Dry Fibers: Control, Treated With Sodium Hydroxide Relaxer Without Cationic Polymer

| Fiber No. | Initial Work Done* (X) | Work Done* After Relaxer (Y) | F20 Index After Relaxer Treatment (% Loss in Tensile Strength) |
|---|---|---|---|
| 2 | 3.170 | 2.540 | 19.87 |
| 3 | 2.250 | 1.840 | 18.22 |
| 4 | 2.230 | 1.780 | 20.18 |
| 6 | 2.300 | 1.910 | 16.96 |
| 8 | 2.950 | 2.340 | 20.68 |
| 10 | 2.440 | 1.950 | 20.08 |
| 12 | 2.490 | 2.010 | 19.28 |
| 18 | 2.790 | 2.320 | 16.85 |
| 19 | 2.190 | 1.790 | 18.26 |
| 20 | 2.870 | 2.230 | 22.30 |
| 21 | 2.400 | 1.830 | 23.75 |
| 22 | 3.130 | 2.390 | 23.64 |
| 25 | 2.880 | 2.250 | 21.88 |
| AVERAGE | | | 20.15 |
| STANDARD DEVIATION (SAMPLE) | | | 2.28 |
| COEFFICIENT OF VARIANCE | | | 11.30 |

*WORK DONE IS IN MILLIJOULES

TABLE 10

Group B Dry Fibers: Experimental, Treated With Sodium Hydroxide Relaxer and Cationic Polymer Betz 1195

| Fiber No. | Initial Work Done* (X) | Work Done* After Relaxer (Y) | F20 Index After Relaxer Treatment (% Loss in Tensile Strength) |
|---|---|---|---|
| 26 | 2.410 | 1.950 | 19.09 |
| 28 | 2.780 | 2.200 | 20.86 |
| 29 | 2.350 | 1.900 | 19.15 |
| 33 | 3.120 | 2.600 | 16.67 |
| 35 | 2.380 | 1.970 | 17.23 |
| 36 | 3.410 | 2.750 | 19.35 |
| 38 | 2.910 | 2.310 | 20.62 |
| 41 | 2.640 | 2.140 | 18.94 |
| 45 | 2.870 | 2.390 | 16.72 |
| 46 | 2.290 | 1.940 | 15.28 |
| 47 | 2.920 | 2.470 | 15.41 |
| 48 | 3.170 | 2.660 | 16.09 |
| 49 | 2.950 | 2.430 | 17.63 |
| AVERAGE | | | 17.93 |
| STANDARD DEVIATION (SAMPLE) | | | 1.87 |
| COEFFICIENT OF VARIANCE | | | 10.45 |

*WORK DONE IS IN MILLIJOULES

As can be seen from TABLES 9 and 10, the average tensile strength loss was more than 12% less for the dry hair fibers treated with the hair strengthening composition of the present invention as compared to those treated with the Control. This reduction in loss of tensile strength means that the hair fibers are stronger and less prone to damage and breakage as compared to hair treated with the Control.

EXAMPLE V

Determination of F20 Index for Wet Fibers Treated with a Guanidine Relaxer and a Merquat 100-Containing Relaxer The F20 Index was determined using the procedure described above under the "WET HAIR FIBER" heading and the Control guanidine relaxer and the Merquat 100-containing guanidine relaxer of TABLE 1, above.

The test results are provided in TABLES 11 and 12, below.

TABLE 11

Group A Wet Fibers: Control, Treated With Guanidine Relaxer Without Cationic Polymer

| Fiber No. | Initial Work Done* (X) | Work Done* After Relaxer (Y) | F20 Index After Relaxer Treatment (% Loss in Tensile Strength) |
|---|---|---|---|
| 1 | 1.460 | 0.631 | 56.78 |
| 3 | 0.983 | 0.363 | 63.07 |
| 4 | 1.210 | 0.425 | 64.88 |
| 5 | 1.270 | 0.567 | 55.35 |
| 6 | 0.990 | 0.376 | 62.02 |
| 7 | 1.240 | 0.337 | 72.82 |
| 8 | 1.610 | 0.612 | 61.99 |
| 9 | 1.180 | 0.553 | 53.14 |
| 10 | 1.040 | 0.365 | 64.90 |
| 11 | 0.877 | 0.290 | 66.93 |
| 12 | 1.110 | 0.424 | 61.80 |
| 13 | 1.010 | 0.404 | 60.00 |
| 14 | 1.080 | 0.384 | 64.44 |
| 15 | 1.160 | 0.460 | 60.34 |
| 16 | 1.020 | 0.416 | 59.22 |
| 17 | 1.220 | 0.404 | 66.89 |
| 18 | 1.410 | 0.708 | 49.79 |
| 19 | 1.050 | 0.427 | 59.33 |
| 20 | 1.610 | 0.570 | 64.60 |
| 21 | 1.060 | 0.469 | 55.75 |
| 22 | 1.340 | 0.482 | 64.03 |
| 23 | 0.936 | 0.355 | 62.07 |
| 24 | 1.240 | 0.413 | 66.69 |
| 25 | 1.120 | 0.442 | 60.54 |
| AVERAGE | | | 61.56 |
| STANDARD DEVIATION (SAMPLE) | | | 5.02 |
| COEFFICIENT OF VARIANCE | | | 8.15 |

*WORK DONE IS IN MILLIJOULES

TABLE 12

Group B Wet Fibers: Experimental, Treated With Guanidine Relaxer and Cationic Polymer Merquat 100

| Fiber No. | Initial Work Done* (X) | Work Done* After Relaxer (Y) | F20 Index After Relaxer Treatment (% Loss in Tensile Strength) |
|---|---|---|---|
| 26 | 1.420 | 0.582 | 59.01 |
| 27 | 1.020 | 0.423 | 58.53 |
| 28 | 0.998 | 0.349 | 65.03 |
| 29 | 1.180 | 0.382 | 67.63 |
| 30 | 1.130 | 0.487 | 56.90 |
| 31 | 0.884 | 0.291 | 67.08 |
| 32 | 1.550 | 0.538 | 65.29 |
| 33 | 1.070 | 0.460 | 57.01 |
| 34 | 1.080 | 0.347 | 67.87 |
| 35 | 0.711 | 0.212 | 70.18 |

TABLE 12-continued

Group B Wet Fibers: Experimental, Treated With Guanidine Relaxer and Cationic Polymer Merquat 100

| | | | |
|---|---|---|---|
| 36 | 1.160 | 0.384 | 66.90 |
| 37 | 0.819 | 0.338 | 58.73 |
| 38 | 1.020 | 0.357 | 65.00 |
| 39 | 1.400 | 0.477 | 65.93 |
| 40 | 0.923 | 0.384 | 58.40 |
| 41 | 1.260 | 0.384 | 69.52 |
| 42 | 1.380 | 0.626 | 54.64 |
| 43 | 0.982 | 0.360 | 63.34 |
| 44 | 1.650 | 0.590 | 64.24 |
| 45 | 1.100 | 0.447 | 59.36 |
| 46 | 1.370 | 0.529 | 61.39 |
| 47 | 0.987 | 0.275 | 72.14 |
| 48 | 1.250 | 0.359 | 71.28 |
| 49 | 1.360 | 0.412 | 69.71 |
| AVERAGE | | | 63.71 |
| STANDARD DEVIATION (SAMPLE) | | | 5.09 |
| COEFFICIENT OF VARIANCE | | | 7.98 |

*WORK DONE IS IN MILLIJOULES

As can be seen from TABLES 11 and 12, the percent loss of tensile strength is actually greater for the hair fibers treated with the Merquat 100-containing guanidine relaxer as compared to the hair fibers treated with the Control guanidine relaxer. The Merquat 100 is commercially available from Calgon Corporation, Pittsburgh, Pa. The Merquat 100 is dially dimethyl ammonium chloride. Thus, the hair fibers treated with the Merquat 100-containing relaxer are more likely to break or be damaged than the hair fibers treated with the Control.

EXAMPLE VI

Determination of F20 Index for Wet Fibers Treated with a Guanidine Relaxer and a Polycare 133-Containing Relaxer The F20 Index was determined using the procedure described above under the "WET HAIR FIBER" heading and the Control guanidine relaxer and the Polycare 133-containing guanidine relaxer of TABLE 1, above. The Polycare 133 is commercially available from Rhone Poulene, Cranbury, Nev. The Polycare 133 is polymethylacrylamidopropyl trimunium chloride.

The test results are provided in TABLES 13 and 14, below.

TABLE 13

Group A Wet Fibers: Control, Treated With Guanidine Relaxer Without Cationic Polymer

| Fiber No. | Initial Work Done* (X) | Work Done* After Relaxer (Y) | F20 Index After Relaxer Treatment (% Loss in Tensile Strength) |
|---|---|---|---|
| 1 | 1.540 | 0.748 | 51.43 |
| 2 | 0.865 | 0.421 | 51.33 |
| 3 | 1.330 | 0.618 | 53.53 |
| 4 | 1.190 | 0.467 | 60.76 |
| 5 | 1.410 | 0.512 | 63.69 |
| 6 | 0.889 | 0.382 | 57.03 |
| 7 | 0.983 | 0.345 | 64.90 |
| 8 | 1.400 | 0.553 | 60.50 |
| 9 | 1.140 | 0.397 | 65.18 |
| 10 | 0.957 | 0.268 | 72.00 |
| 11 | 1.590 | 0.619 | 61.07 |
| 12 | 1.360 | 0.602 | 55.74 |

TABLE 13-continued

| Group A Wet Fibers: Control, Treated With Guanidine Relaxer Without Cationic Polymer | | | |
|---|---|---|---|
| 13 | 1.030 | 0.371 | 63.98 |
| 14 | 1.090 | 0.408 | 62.57 |
| 15 | 1.540 | 0.672 | 56.36 |
| 16 | 1.540 | 0.633 | 58.90 |
| 17 | 1.200 | 0.453 | 62.25 |
| 18 | 1.560 | 0.541 | 65.32 |
| 19 | 1.580 | 0.783 | 50.44 |
| 20 | 1.190 | 0.515 | 56.72 |
| 21 | 1.250 | 0.517 | 58.64 |
| 22 | 0.941 | 0.557 | 40.81 |
| 23 | 1.050 | 0.337 | 67.90 |
| 24 | 1.090 | 0.513 | 52.94 |
| 25 | 0.796 | 0.327 | 58.92 |
| AVERAGE | | | 58.92 |
| STANDARD DEVIATION (SAMPLE) | | | 6.63 |
| COEFFICIENT OF VARIANCE | | | 11.25 |

*WORK DONE IS IN MILLIJOULES

TABLE 14

| Group B Wet Fibers: Experimental, Treated With Guanidine Relaxer and Cationic Polymer Polycare 133 | | | |
|---|---|---|---|
| Fiber No. | Initial Work Done* (X) | Work Done* After Relaxer (Y) | F20 Index After Relaxer Treatment (% Loss in Tensile Strength) |
| 26 | 1.440 | 0.672 | 53.33 |
| 27 | 1.000 | 0.479 | 52.10 |
| 28 | 1.310 | 0.582 | 55.57 |
| 29 | 1.200 | 0.397 | 66.92 |
| 30 | 1.390 | 0.484 | 65.18 |
| 31 | 1.010 | 0.408 | 59.60 |
| 32 | 0.987 | 0.317 | 67.88 |
| 33 | 1.610 | 0.652 | 59.50 |
| 34 | 1.170 | 0.468 | 60.00 |
| 35 | 0.964 | 0.266 | 72.41 |
| 36 | 1.590 | 0.604 | 62.01 |
| 37 | 1.320 | 0.517 | 60.83 |
| 38 | 0.972 | 0.337 | 65.33 |
| 39 | 1.240 | 0.439 | 64.60 |
| 40 | 1.600 | 0.623 | 61.06 |
| 41 | 1.680 | 0.778 | 53.69 |
| 42 | 1.050 | 0.342 | 67.43 |
| 43 | 1.440 | 0.515 | 64.24 |
| 44 | 1.510 | 0.670 | 55.63 |
| 45 | 1.350 | 0.502 | 62.81 |
| 46 | 1.200 | 0.400 | 66.67 |
| 47 | 1.320 | 0.524 | 60.30 |
| 48 | 0.969 | 0.279 | 71.21 |
| 49 | 1.240 | 0.574 | 53.71 |
| 50 | 0.793 | 0.302 | 61.92 |
| AVERAGE | | | 61.75 |
| STANDARD DEVIATION (SAMPLE) | | | 5.71 |
| COEFFICIENT OF VARIANCE | | | 9.24 |

*WORK DONE IS IN MILLIJOULES

As can be seen from TABLES 13 and 14, the percent loss of tensile strength is actually greater for the hair fibers treated with the Polycare 133-containing guanidine relaxer as compared to the hair fibers treated with the Control guanidine relaxer. Thus, the hair fibers treated with the Polycare 133-containing relaxer are more likely to break or be damaged than the hair fibers treated with the Control.

It is presently theorized that the above-described advantages are achieved because the swelling of the hair fiber by the hair swelling component permits the cationic polymer to be affixed to the hair. The cationic polymer can be affixed by mechanical or chemical bonding to the hair. The swelling of the hair permits the cationic polymer to penetrate into the cortex of the hair fiber and form an elastic network in the cortex. Even after the hair is rinsed, the polymer is locked inside the hair to increase the tensile strength of the hair fiber due to the elastic nature of the cationic polymer.

What is claimed is:

1. A method of strengthening hair in need of strengthening, the method comprising the steps of:

applying a hair swelling component to hair in need of strengthening; and applying a cationic polymer that is the reaction product of a lower dialkylamine ($C_1$–$C_3$), a difunctional epoxy-type reactant and a third reactant selected from the group consisting of ammonia, primary amines, alkylene diamines having two to six carbon atoms and polyamines to the hair.

2. The method of claim 1 wherein the applying steps are performed simultaneously.

3. The method of claim 1 further comprising the step of contacting the hair with the hair swelling component for a time period sufficient to swell the hair.

4. The method of claim 3 further comprising the steps of:

penetrating the swollen hair with an aliquot of the applied cationic polymer; and affixing the aliquot to the swollen hair.

5. The method of claim 4 further comprising the step of removing the applied cationic polymer that has not penetrated the swollen hair.

6. The method of claim 1 further comprising the step of removing or neutralizing the hair swelling component.

7. The method of claim 1 further comprising the step of providing elasticity to the hair with the cationic polymer.

8. The method of claim 1 further comprising the steps of:

affixing cationic polymer to the swollen hair; and removing from the hair cationic polymer that is not affixed to the hair.

* * * * *

UNITED STATES PATENT AND TRADEMARK OFFICE
CERTIFICATE OF CORRECTION

PATENT NO. : 5,641,478
DATED : June 24, 1997
INVENTOR(S) : Syed et al.

It is certified that error appears in the above-identified patent and that said Letters Patent is hereby corrected as shown below:

In Column 5, Line 6, please delete Line 6 and insert the following --I. F20 Index = [(X-Y)/X]x100--
In Column 9, Line 47, please delete "0.949" and insert the following --0.849--

Signed and Sealed this

Twenty-third Day of December, 1997

*Attest:*

BRUCE LEHMAN

*Attesting Officer*     *Commissioner of Patents and Trademarks*